United States Patent
Bailey et al.

(12)

(10) Patent No.: US 6,649,408 B2
(45) Date of Patent: Nov. 18, 2003

(54) MICRODROPLET CELL CULTURE TECHNIQUE

(75) Inventors: Charles L. Bailey, Fayetteville, TN (US); Ken Alibek, Alexandria, VA (US)

(73) Assignee: George Mason University, Fairfax, VA (US)

(*) Notice: Subject to any disclaimer, the term of this patent is extended or adjusted under 35 U.S.C. 154(b) by 0 days.

(21) Appl. No.: 09/805,464

(22) Filed: Mar. 14, 2001

(65) Prior Publication Data

US 2002/0022265 A1 Feb. 21, 2002

Related U.S. Application Data

(60) Provisional application No. 60/191,771, filed on Mar. 24, 2000.

(51) Int. Cl.[7] .................................................. E12N 5/00
(52) U.S. Cl. ..................... 435/325; 435/243; 435/173.1; 435/289.1
(58) Field of Search ................................. 435/325, 243, 435/173.1, 289.1

(56) References Cited

U.S. PATENT DOCUMENTS

| 4,242,447 A | * | 12/1980 | Findl et al. |
| 4,399,219 A | * | 8/1983 | Weaver |
| 4,959,301 A | * | 9/1990 | Weaver et al. |
| 5,925,511 A | * | 7/1999 | Fuhr et al. |

* cited by examiner

*Primary Examiner*—Leon B. Lankford, Jr.
(74) *Attorney, Agent, or Firm*—Whitham, Curtis & Christofferson, PC

(57) ABSTRACT

The present invention comprises a novel culture method and device in which living cells are cultured in a plurality of individual microdroplets that are immobilized and isolated within a matrix of hydrophobic particles. The hydrophobic particles adhere to inoculated microdroplets of media, isolating the microdroplets in an aseptic microenvironmet. The plurality of individual microdroplets provide and optimal environment for the concentrated growth of cultured cells contained therein.

12 Claims, 2 Drawing Sheets

FIG. 2

CERAMIC OXIDE PARTICLES → COATING VESSEL (MEANS FOR CREATING INOCULATED MICRODROPLETS) ← INOCLUATED LIQUID MEDIA

BATCH CULTURE / CONTINUOUS FLOW CULTURE

MICRODROPLET CELL CULTURE TECHNIQUE

DESCRIPTION

This application claims the benefit of U.S. Provisional Application No. 60/191,771, filed Mar. 24, 2000.

BACKGROUND OF THE INVENTION

1. Field of the Invention

The present invention generally relates to the cultivation and growth of cells on laboratory, pilot plant, or industrial scales and, more particularly, to the cultivation and growth of cells in a plurality of individual microdroplets of liquid media which are interspersed within a matrix of hydrophobic microparticles.

2. Background Description

The culturing of microbial and animal or plant cells are crucial processes that are essential to the production of a wide array of useful chemical and biochemical products. Living cells are employed in such processes because they provide the essential elements necessary to economically synthesize many commercially valuable metabolic products.

Typically, growing cells are cultured either in liquid media (submerged cultivation) or on the surface of a solid nutrient(surface cultivation). Microorganisms such as bacteria and fungi can be cultured in either the surface or submerged method. Eukaryotic cells can be cultured in a submerged or suspended cell culture in rolling flasks or, where cell surface attachment is necessary, cells are grown to confluence in tissue culture flasks with liquid nutrient media placed above the cells. A suitable nutrient medium for microorganisms typically includes a carbon and energy source, an assimilable nitrogen source, oxygen (usually derived from surrounding air), and suitable pH conditions and additional factors which vary for a given microorganism, as one skilled in the art can readily appreciate.

With the surface method, nutrients are absorbed from contact with the media under the culture, oxygen is provided through contact with the air above the culture, and inhibitory metabolites seep down and away from the culture. Surface cultivation of microorganisms has the advantageous features of providing a plentiful oxygen source from the surrounding air and efficient removal of inhibitory metabolites through absorption from the surface medium. Also, contamination of surface culture can be relatively confined to a minimal surface area or a growing culture.

On the negative side, surface cultivation of microorganisms is not amenable to large scale production. The process of filling and inoculating numerous individual plates or dishes with culture and then individually harvesting each plate is extremely labor intensive. Furthermore, the storage of solid surface plates or dishes inoculated with microorganisms requires significant allocations of space in sophisticated incubators.

With the submerged method, a microorganism is cultured throughout the liquid media. Nutrients are absorbed from contact with the media surrounding the individual microorganisms, oxygen and are provided by various means of aeration that one skilled in the art can readily appreciate, and metabolites seep out and into the media. Usually, the nutrient media is also stirred continually, in order to evenly distribute the microorganisms.

The submerged cultivation process has the beneficial advantages of being less labor and space intensive than the surface method and can be used to produce large batches of cells in a relatively small space. The submerged method is thus the method of choice currently employed in most pilot and industrial scale production of cultured microorganisms and cells.

The submerged cultivation method does, however, require an extensive investment in equipment necessary for the large scale production of cell cultures. In addition, the end products that are the object of large scale submerged cultivation (i.e., the intracellular or extracellular metabolic products of cell and microbe growth) usually require further purification and concentration either from the liquid media or the cells therein. This additional isolation step is necessary because the concentration of product in the media is limited by the metabolites released into the media and the limited solubility of oxygen and/or other gases in the media.

Another major drawback to the large scale submerged cultivation method is the greater risk and effects of contamination that this method entails. In submerged cultivation, the complexity of the equipment necessary for bacterial fermentation systems, for example, provides more opportunities for a contamination event when compared to the surface growth methodology. Furthermore, once a culture is contaminated, the contamination quickly spreads throughout the agitated liquid media, resulting in the destruction of the entire batch of a culture.

SUMMARY OF THE INVENTION

It is therefore an object of the invention to provide for the growth of a microbe or cell culture with a hybrid method that both combines the beneficial features of submerged and surface cultivation while eliminating some of the negative features inherent in both procedures.

It is another object of the invention to provide an apparatus for the sterile growth of a cell culture in a collection of individual microdroplets. The invention provides for the growth of both prokaryotic and eukaryotic organisms. The invention is particularly suited to the aseptic cultivation of human, animal, plant or microbial cell populations.

It is further an object of the present invention to provide a method and apparatus for cell culture that substantially reduces the capital and labor costs of producing cell culture on a large scale.

It is further an object of the present invention to provide a method and apparatus for cell culture that substantially reduces the risks of contamination by opportunistic organisms.

It is further an object of the invention to provide a method and apparatus for cell culture that can be performed in a continuous flow or batch process.

It is further an object of the invention to provide a method for cell culture that eliminates the need to concentrate organisms following cell growth.

It is further an object of the invention to provide a method and apparatus for cell culture that substantially increases the yield of products such as enzymes or proteins that are produced by the particular organisms cultured.

It is further an object of the present invention to provide a cell culture method that substantially increases the yield of products produced from genetically engineered cells such as, for example, vaccine products, biopesticides, antibiotics, and the like.

It is further an object of the invention to provide a method and apparatus for cell culture with substantially enhanced simplicity of operation and portability.

According to the invention, cells are cultivated in a plurality of individual microdroplets of liquid media. These microdroplets are created by aerosolizing liquid media that has been inoculated with the cells of interest and coating the aerosolized droplets with hydrophobic particles of solid material, such as silicon dioxide, for example. The individual microdroplets are stabilized within the hydrophobic solid particles, thereby providing a large number of small cell culture reactors. The coated microdroplets each provide a sterile environment for the individual microdroplets contained within the culture. Furthermore, the individual microdroplets each provide an optimum microenvironment with a reduced effect of potentially inhibitory metabolites and optimal accessability to aeration, resulting in substantial increases in the concentration of cells per liquid volume.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is a schematic representation of the various steps employed in one embodiment of the invention.

DETAILED DESCRIPTION OF PREFERRED EMBODIMENTS OF THE INVENTION

Figure 1:
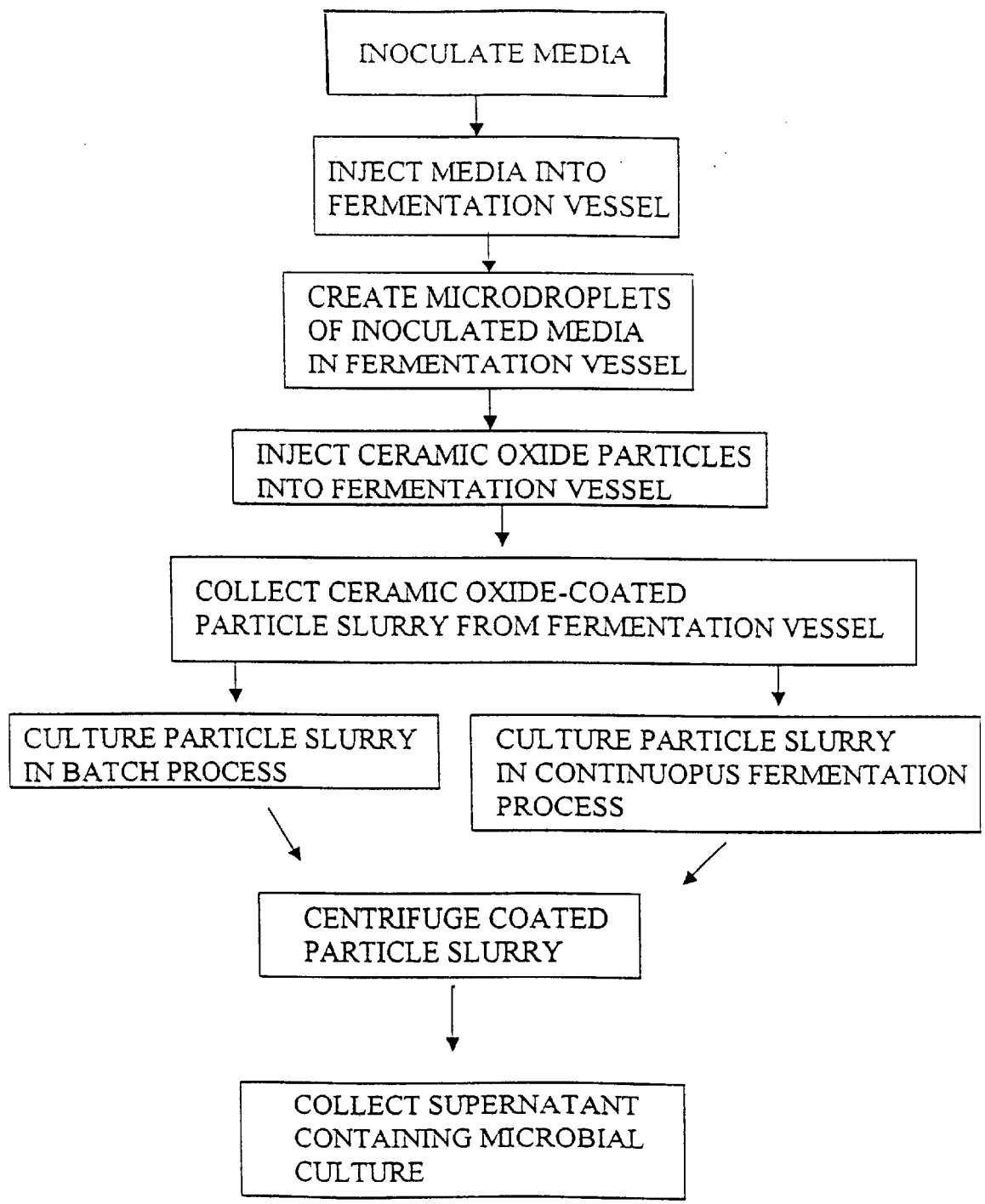
FIG. 1 is a flow chart diagrammatically representing the generalized series of procedures employed in the practice of the invention.

The present invention provides a generalized method and apparatus for aseptically culturing a plurality of microdroplets of media that are inoculated with a given cell type that is to be cultured. Each individual microdroplet provides an individual microenvironment that is isolated from the surrounding microdroplets. In such a manner, each microdroplet is protected from contamination by any adjacent microdroplets. In addition, the apparatus and methods of the present invention provide for concentrated growth of cells in minimal amounts of liquid medium, without the need for extensive further concentration of cells or their metabolic products.

Referring now to the drawings, and more particularly to FIG. 1, there is shown a flow chart of the process that is the object of the present invention. Liquid media is inoculated with a given cell strain, which can be a prokaryotic or eukaryotic cell, either of which may be additionally infected with a virus, transformed with a heterologous DNA expression vector, or otherwise genetically engineered to produce a given substance with techniques that are well known within the art. It is also within the scope of the present invention that cells that produce important chemical and biochemical products without any genetic alterations can be grown with the apparatus and methods of the invention.

In the practice of the present invention, liquid media is inoculated in an aseptic fashion with a cell type that is to be cultured. Referring now to FIG. 2, the inoculated media is then introduced through a first opening into a coating vessel of the present invention, for example, in one embodiment by means of a peristaltic pump, through an entry port. The coating vessel provides an environment in which individual microdroplets of inoculated media can be encased by hydrophobic solid particles. Once the microdroplets are formed and added to the coating vessel, dry hydrophobic powder composed of a plurality of particles of, for example, a hydrophobic ceramic, are introduced into the vessel where the coating process then occurs. The hydrophobic particles intercalate with and adhere to the individual microdroplets, preventing the microdroplets from becoming a confluent liquid, thereby creating a plurality of individual microdroplet cultures, each containing an isolated droplet of growing cells. The resulting product is a slurry-like material that has a semi liquid consistency, due to the fact that the individual microdroplets are prevented from re-aggregating as a confluent liquid. Once the coated hydrophobic particles are formed, they are collected and removed through narrow slotted openings located at the bottom of the coating vessel. The coated microdroplets are then cultured either in a batch or continuous flow process.

It is contemplated in the practice of the present invention that the timing and means of introducing the inoculated media and hydrophobic particles can be varied without departing from the scope of the present invention. For example, the media may be introduced through means other than a peristaltic pump and an entry port, for example, via a spray nozzle. In addition, it is only required that the hydrophobic particles be introduced into the coating vessel at a time such that they are able to homogeneously mix with the microdroplets of liquid media. This time may be varied without departing from the scope of the invention. For example, as discussed further infra, the hydrophobic particles may be introduced into the coating vessel prior to, simultaneous with, or subsequent to formation of the microdroplets of inoculated culture. The only limitation on this aspect of the invention is that the hydrophobic particles must be able to surround and adhere to the microdroplets after they are formed.

In one embodiment of the invention, the inoculated media is converted into microdroplets prior to introduction into the coating vessel. Such a process is enabled by introducing the inoculated media via a spray nozzle that dispenses individual microdroplets into the vessel. It is not essential to the practice of the invention that the microdroplets be created prior to the introduction of the droplets into the coating vessel. Thus, in yet another embodiment, the microdroplets are created after the inoculated liquid media is introduced into the coating vessel. Ferromagnetic particles are sterilized and introduced into a non-magnetic mixing/coating vessel. Electromagnetic inductors are mounted in parallel on either side of the coating vessel. Activation of the electromagnetic inductors causes an electromagnetic field to exist within the vessel. Oscillations of this electromagnetic field are induced by the inductors. The ferromagnetic particles orient along and follow the field lines of the electromagnetic field and follow the oscillations of the field. The rapid motion of the field and particles vigorously mixes the hydrophobic particles and liquid media, inducing the formation of droplets.

The size of the microdroplets will vary, with an optimum size for the cultivation of microorganisms, for example, usually being between 0.5 and 2.0 mm in diameter. Sizes within this range have been found to result in high concentrations of microorganisms per microdroplet. It should readily be understood by one skilled in the art, however, that the optimal size of microdroplet will vary, depending on such factors as the growth rate of the cultured cell type, the amount of optimal aeration for a given cell type, the most effective cell density for production of a given metabolite, and the like.

The size of individual microdroplets can be regulated by adjusting such factors as the size of the nozzle or portal delivering the liquid or aerosolized media, the volume of the vessel, the speed at which the various components are added, the power and frequency of electromagnetic induction (in one embodiment of the invention), and the type of hydrophobic particle utilized, for example.

In one particular embodiment of the invention, the vessel is contained in a refrigerated environment to prevent the rapid random motion of the electromagnetic process from destroying the inoculated microdroplets with excessive heat.

Once the microdroplets of inoculated media have formed, the hydrophobic particles can then intercalate between and around individual microdroplets, creating a semi-liquid slurry comprising a matrix of interspersed microdroplets of inoculated culture and hydrophobic particles. In one embodiment of the invention, the particles are pumped into the coating vessel while the ferromagnetic particles and liquid media are agitated, resulting in the simultaneous agitation and mixing of the hydrophobic particles along with the microdroplets. In another embodiment, the hydrophobic particles are introduced through a second opening positioned such that the particles encounter the aerosolized microdroplets of inoculated media as the droplets enter the vessel.

The hydrophobic particles can be introduced into the vessel by a variety of methods well known within the art, for example, by forced flow with the assistance of an air pump. Introduction of the coating particles can be through the same opening used for the introduction of the inoculated media or through a second opening. The use of two different openings for the media and coating particle introduction may have the advantage of allowing for easier process controls.

In one embodiment of the invention, the hydrophobic particles comprises a powder of silicon dioxide. It can readily be seen by one skilled in the art, however, that the hydrophobic particles can alternatively comprise other hydrophobic ceramic particles (e.g., possibly aluminum oxides and zinc oxides).

In a particularly preferred embodiment, the silicon dioxide particles are Aerosil 300, produced by Brenntag N.V. of Belgium. In another preferred embodiment, the silicon dioxide particles are selected from the group comprising the AEROSIL series of powders manufactured by the Degussa-hüls Corporation (i.e., AEROSIL R 104, AEROSIL R 106, AEROSIL R 202, AEROSIL R 805, AEROSIL R 812, AEROSIL R812.S, AEROSIL R 972, AEROSIL R 974, and AEROSIL R.8200). Other silicon dioxide particles are contemplated and within the scope of the invention. The choice of silicon dioxide particles will vary depending on the organism to be cultured and the amount of aeration required. In general, silicon dioxide particles that are useful in the practice of the present invention will be hydrophobic and have a surface area between 50 and 380 meters$^2$ per gram of weight.

It is contemplated within the practice of the invention that the percent composition of coating particles to inoculated medium will vary, depending on, but not limited to, such factors as the cell type, the size of the individual microdroplets, and the desired final density and phase of growth that is the objective of the particular culture. In one embodiment of the invention that the ratio of individual coating particles to cultured inoculum may be within a range of 99:1 and 1:99. In one preferred embodiment of the invention, the ratio individual coating particles to cell inoculum to will be within a range of 1:2 to 2:1.

Once the microdroplets are formed and coated, they are evacuated from the coating vessel through narrow slotted openings at the bottom of the vessel. In one particular preferred embodiment, the slotted openings will be between 1.5–2.0 mm wide but may vary depending on the size of the microdroplets formed. The microdroplets can be as little as 10 to 20 microns, so long as the initial inoculum is dense enough to ensure each microdroplet contains inoculated medium. The microdroplets can be much larger, with diameters greater than 2.5 mm, so long as the hydrophobic particles are able to maintain the media in individual droplet form. Accordingly, the slots for removal can also be designed to be the same as whatever size the microdroplets are or slightly larger.

In most cases, the space between the coated microdroplets provides adequate aeration of the cell culture. It is a particularly useful and beneficial feature of the present invention that the space which exists between individual coated microdroplets provides an optimum environment for the concentrated growth of cell cultures. The adequate aeration provided with the present invention allows the growing cultures to make optimal use of the liquid media contained within each microdroplet.

It can readily be seen by one skilled in the relevant art, however, that various means can be employed to provide the growing microdroplet culture with supplemental oxygen and/or other gases to optimize the aeration conditions for a given cell culture. For example, a fermentation vessel or zone may be provided with a port opening onto the vessel or zone through which exogenous molecular oxygen may be pumped via conduits and means to transport the gas. Additionally, the fermentation vessel or zone may further be equipped with a second port opening for removal of gases during the fermentation process.

In one embodiment of the invention, the cultured cells will be microorganisms. Fermentation of microorganisms can proceed via a batch process or a continuous fermentation process. In the case of batch fermentation, the microdroplets are collected and grown in a fermentation vessel. In a continuous fermentation process, the coated microdroplets are collected from the slots at the bottom of the coating vessel and are grown in long conduits that constitute a fermenting zone. The particular fermentation method used to culture the microdroplets is not critical to the practice of the present invention.

As can readily be appreciated by one skilled in the art, it will not always be necessary or preferable to separate the hydrophobic particles away from the liquid cell culture following cell growth. For example, since silicon dioxide is frequently utilized in soil treatment, there is no need to remove the silicon dioxide from cell cultures that are grown for the purposes of soil treatment. Furthermore, since the hydrophobic particles limit the potential for the spread of contamination, it may be desirable to maintain cultivated cells within the Individual hydrophobic microdroplets for storage purposes.

It is a particularly beneficial feature of a preferred embodiment of the present invention that the enhanced aeration of cultured cells, combined with the efficient removal of metabolites, allow for microbial cultures to divide to a density that consumes all of the available liquid present in a microdroplet. Thus, in a preferred embodiment of the invention there is no need to (1) concentrate cultures or (2) remove the hydrophobic particles from the microdroplet culture. When all of the liquid media is consumed, the hydrophobic particles disassociate from the cell cultures, allowing the cells to interact directly with the surrounding environment.

Alternatively, once cell growth is complete, the liquid media can be isolated away from the hydrophobic particles through a simple centrifugation step. As can readily be appreciated by one skilled in the art, the time and force of centrifugation will vary depending on the organism and hydrophobic particle employed in the process. The silicon dioxide particles can be sterilized and re-used in another microdroplet cultivation process.

EXAMPLE I

Bioremediation

The present invention can be used to generate large quantities of a bacterial species to be used for bioremediation methodologies. Many examples of decontamination through bioremediation exist, including bioremediation with Pseudomonas, Nitrobacter and Baccillus strains. See, for example, U.S. Pat. No. 6,025,152 to Hiatt for relevant examples of bacterial bioremediation organisms.

The portability of the present invention allows the production of large numbers of bacteria at the site of need. In addition, the bacteria can be grown on site and released still encased within the hydrophobic particles. Only upon consumption of the nutrient media will the hydrophobic particles dissociate and the bacteria then integrate into the contaminated site. This process ensures that the bacteria will be present in maximum quantities when introduced into the contamination site.

In a process that employs many of the aspects involved in bioremediation, the present invention can similarly be used In the process of bio-prospecting. This process involves the cultivation of microorganisms used for leaching many precious and rare metals from different ores. Micrорganisms such as *Thiobacillus thiooxidans* and others are used industrially to oxidize sulfide minerals to promote the process of metal leaching. The following metals might be leached using this process: gold, silver, cooper, germanium, gallium, selenium, indium and many others. Since this method does not require a complicated equipment and high energy consumption, the installation for cultivation can be built at a site of mining.

EXAMPLE II

Production of Vaccine Products

The present invention is suitable to the large scale production of recombinant bacteria or tissue culture cells that have been genetically engineered to produce an antigen or antigens that are effective vaccine products. For a relevant example of bacterial vaccine production, see U.S. Pat. No. 6,036,593 to Ryan, et al. Bacterial or mammalian cells may be cultivated in a plurality of microdroplets to high densities, eliminating the need to further concentrate the recombinant products of the cultured cells.

The present invention can be adapted to the large scale growth of recombinant organisms such as yeast cells that have similarly been modified to produce pharmaceutically active proteins such as insulin and other growth factors, as in U.S. Pat. No. 4,775,622 to Hitzeman, et al.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A cell culture method comprising the steps of:

introducing liquid media inoculated with cells to be cultured into a vessel;

converting the inoculated liquid media into individual microdroplets;

introducing a sufficient quantity of hydrophobic particles in the form of a dry powder into the vessel to coat the individual microdroplets; and growing the cells within the individual microdroplets.

2. The cell culture method of claim 1 further comprising the step of recovering the cultured cells from the individual microdroplets.

3. The cell culture method of claim 1 wherein the converting step comprises:

adding ferromagnetic particles to the vessel;

applying an electromagnetic field within the vessel, thereby causing the random circulation of the ferromagnetic particles throughout the vessel.

4. The process of claim 1 wherein the cultured cells are microbial cells.

5. The process of claim 1 where the cultured cells are fungal cells.

6. The process of claim 1 wherein the cells are bacterial cells.

7. The process of claim 1 wherein the cells are eukaryotic cells.

8. The process of claim 1 wherein the cells are insect cells.

9. The process of claim 1 wherein the hydrophobic particles are silicon dioxide particles.

10. The process of claim 1 wherein the ratio of inoculated media to hydrophobic particles comprises a range between 1:2 and 2:1.

11. The process of claim 1 wherein the growing step further comprises the step of providing the microdroplets with exogenous gas.

12. The process of claim 10 wherein the exogenous gas is molecular oxygen.

* * * * *